United States Patent
Stamberg

(10) Patent No.: US 9,409,000 B2
(45) Date of Patent: Aug. 9, 2016

(54) BALLOON WITH FIBERS FOR TREATMENT OF BLOOD VESSELS

(71) Applicant: Abbott Cardiovascular Systems Inc., Santa Clara, CA (US)

(72) Inventor: Barbara E. Stamberg, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 582 days.

(21) Appl. No.: 13/709,716

(22) Filed: Dec. 10, 2012

(65) Prior Publication Data

US 2014/0163525 A1 Jun. 12, 2014

(51) Int. Cl.
*A61M 31/00* (2006.01)
*A61M 25/10* (2013.01)

(52) U.S. Cl.
CPC ............ *A61M 25/10* (2013.01); *A61M 25/104* (2013.01); *A61M 2025/105* (2013.01); *A61M 2025/1081* (2013.01); *A61M 2025/1086* (2013.01)

(58) Field of Classification Search
CPC .............. A61M 25/10; A61M 25/104; A61M 2025/105; A61M 2025/1081; A61M 2025/1086
USPC ................ 604/103.02, 509, 103.01, 103.08
See application file for complete search history.

(56) References Cited

U.S. PATENT DOCUMENTS

| 5,370,653 | A | 12/1994 | Cragg | |
|---|---|---|---|---|
| 5,501,663 | A | 3/1996 | Hattler | |
| 5,882,332 | A | 3/1999 | Wijay | |
| 7,077,836 | B2 | 7/2006 | Lary | |
| 2004/0064093 | A1* | 4/2004 | Hektner | A61M 25/104 604/103.01 |
| 2004/0087902 | A1* | 5/2004 | Richter | A61M 25/10 604/103.02 |
| 2009/0198216 | A1* | 8/2009 | Muni | A61B 17/24 604/514 |
| 2011/0104061 | A1* | 5/2011 | Seward | A61K 9/0019 424/9.1 |
| 2011/0166516 | A1* | 7/2011 | Orr | A61M 25/10 604/103.01 |
| 2012/0303048 | A1* | 11/2012 | Manasse | A61F 2/2436 606/167 |

* cited by examiner

*Primary Examiner* — Theodore Stigell
*Assistant Examiner* — Tiffany Legette
(74) *Attorney, Agent, or Firm* — Randy Shen; Blakely, Sokoloff, Taylor & Zafman LLP

(57) ABSTRACT

The disclosed subject matter describes systems and methods of delivering a therapeutic agent, such as a sclerosing agent, to the walls of a blood vessel to perform sclerotherapy. In an exemplary embodiment a catheter includes a balloon having an inner and outer surface defining a wall, and an interior volume with an unexpanded and expanded configuration and a plurality of fibers extending from the outer surface of the balloon wall. In another exemplary embodiment, a balloon catheter comprises a catheter having a balloon with an unexpanded and an expanded configuration, and a retractable sheath disposed on the exterior surface of the balloon, wherein the sheath has an inner surface and an outer surface, and further wherein a plurality of fibers outwardly extend from the outer surface of the sheath.

12 Claims, 4 Drawing Sheets

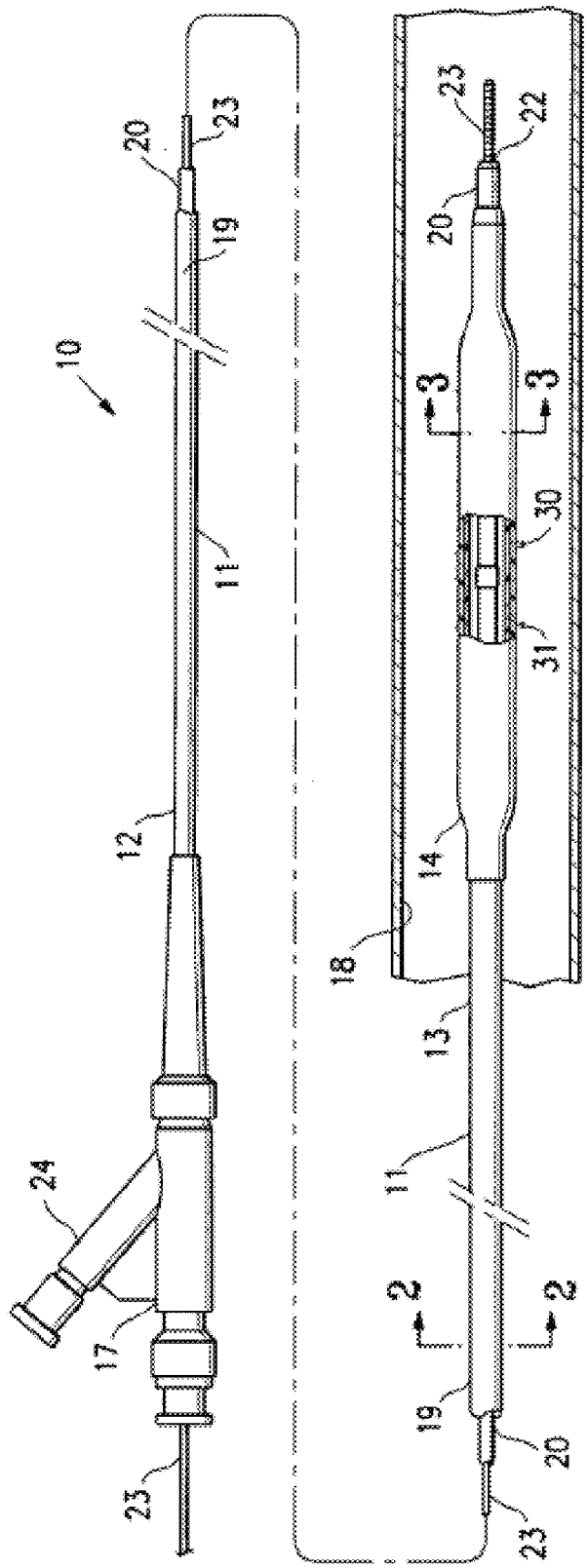
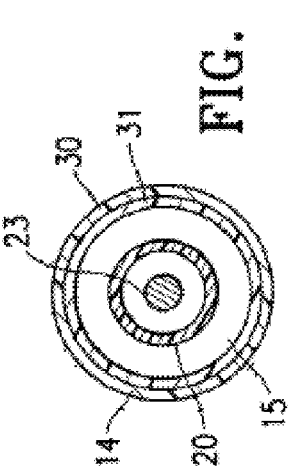
FIG. 1
FIG. 2
FIG. 3

BALLOON WITH FIBERS FOR TREATMENT OF BLOOD VESSELS

FIELD OF THE DISCLOSED SUBJECT MATTER

The disclosed subject matter relates to treating blood vessels using a therapeutic agent. More particularly, the disclosed subject matter relates to a medical device configured to deliver an agent at select locations within a patient's blood vessel. An exemplary embodiment of such a device includes a balloon with fibers extending therefrom and configured to deliver a therapeutic agent, such as a sclerosing agent, to the walls of a blood vessel to perform sclerotherapy.

BACKGROUND OF THE DISCLOSED SUBJECT MATTER

Varicose veins are blood vessels that have become enlarged and tortuous over a period of time. Most commonly, varicose veins occur in veins on the leg, although they can occur elsewhere. Varicose veins are caused when the leaflets of the valves in the blood vessel no longer close properly, thereby allowing for retrograde flow and pooling of blood.

Varicose veins are most common in the superficial veins of the legs. They are often painful and can produce ankle swelling, skin discoloration, dermatitis or venous eczema, cramps, and skin tightness around the affected region. In severe cases of varicose veins, complications may occur. For example, the varicose veins may become very painful and hinder a person's ability to work or perform routine motions and exercises. Skin conditions including itching and flaking associated with varicose veins may also predispose a person to skin loss. Development of serious conditions like blood clots, carcinoma, or sarcoma, may also occur.

As a result, many non-surgical and surgical treatments of varicose veins have been developed. Non-surgical treatments include sclerotherapy, elastic stockings, elevating the legs, and exercise. The traditional surgical treatment has been vein stripping to remove the affected veins. Newer surgical treatments include ultrasound-guided foam sclerotherapy, radiofrequency ablation and endovenous laser treatment.

Sclerotherapy is a commonly performed non-surgical treatment for treating varicose veins in which a sclerosing agent is injected into the veins to make them shrink. Complications of sclerotherapy are rare but can include blood clots and ulceration. Furthermore, conventional sclerotherapy techniques often result in incomplete and/or uneven treatment along the length of the patient's blood vessel.

In order for sclerotherapy to be effective, it is necessary to evenly dispense the sclerosing agent throughout the wall of the vein without using toxic levels of the sclerosing agent. This is not particularly difficult for the smaller veins. However, it is quite difficult or nearly impossible in larger veins. When a larger vein is injected with a sclerosing agent, the sclerosing agent is quickly diluted by the large volume of blood in the vein. As a result, the vein is sclerosed only in the region of the injection. If the procedure is continued, and the injections are far apart, the vein can become disfigured. The problem cannot be cured by injecting a more potent solution of sclerosing agent, because the sclerosing agent may become toxic at such a concentration. Therefore, a need exists for a system that is capable of delivering a sclerosing agent to the varicose vein walls that prevents the dilution of the sclerosing agent into the blood.

SUMMARY OF DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a medical device configured for localized delivery a therapeutic agent comprising balloon catheter comprising a catheter having at least one lumen extending therethrough, a balloon having a body including an inner and outer surface defining a wall, wherein the body defines an interior volume in fluid communication with the at least one lumen and having an unexpanded and expanded configuration, and a plurality of fibers extending from the outer surface of the balloon wall. In some embodiments, the fibers are elongate and hollow and are configured to deliver a therapeutic agent.

In other embodiments, the balloon is constructed from biodegradable materials. The surface of the balloon may be blood phobic or alcohol phylic. To inflate the balloon, an inflation fluid containing a sclerosing agent (e.g., ethanol) may be utilized.

Prior to inflation, the balloon may contain a sheath configured to be slidable over the balloon in its unexpanded configuration. The sheath is configured to keep the fibers proximate to the balloon's surface. The sheath can be removed or refracted prior to the balloon's inflation and subsequently advanced over the fibers after deflation of the balloon.

In some embodiments, the balloon contains perforations in its wall. Preferably, the perforations are approximately 20 microns in diameter.

In another exemplary embodiment, a catheter is provided having at least one lumen extending therethrough, a balloon having an unexpanded and an expanded configuration, the balloon defining a interior volume in fluid communication with the at least one lumen when in the expanded configuration, wherein the balloon is configured for expansion between an unexpanded and expanded configuration, and a flexible sheath disposed on the exterior surface of the balloon, wherein the sheath comprises an inner surface and an outer surface, and further wherein a plurality of fibers outwardly extend from the outer surface of the sheath. Additionally, the sheath can be formed from an elastomeric material and is configured to have an unexpanded and expanded configuration.

A method of performing sclerotherapy on a blood vessel is also described herein. First, the blood vessel is occluded using a first occlusion element and a second occlusion element to define a portion of the blood vessel that is to be sclerosised. A balloon having a plurality of fibers extending laterally from the balloon is inserted into the occluded portion of the blood vessel. An inflation fluid, including a sclerosing agent, is introduced into the balloon, thereby causing the sclerosing agent to be delivered to the walls of the blood vessel by the fibers. Next, the sclerosing agent and the balloon are removed from the occluded blood vessel followed by the occluding elements. The vein may then be compressed with a bandage to promote necrosis of the blood vessel.

The occluding elements may be any known in the art including, but not limited to, a balloon, a gel, a bellows, or a permanent occlusion device. In some embodiments, the occluding elements may be self-expanding.

Preferably, the balloon is delivered into the blood vessel by a catheter. The blood vessel may be any that requires sclerotherapy, such as a varicose vein or a hemhorrhoid.

It is to be understood that both the foregoing general description and the following detailed description are exemplary and are intended to provide further explanation of the disclosed subject matter.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

FIG. 1 is an elevational view, partially in section, of an over-the-wire type balloon catheter embodying features of the invention;

FIG. 2 and FIG. 3 are transverse cross sectional views of the catheter of FIG. 1, taken along lines 2-2 and 3-3, respectively;

DETAILED DESCRIPTION OF EXEMPLARY EMBODIMENTS

Figure 4:
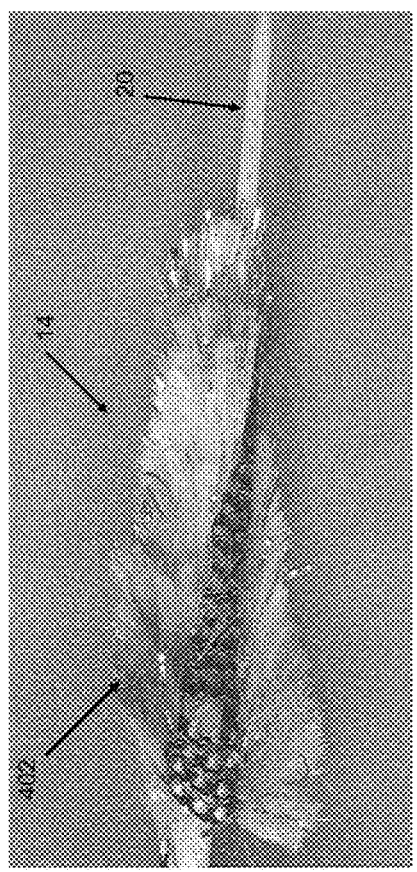
FIG. 4 illustrates an enhanced view of the balloon depicted in FIG. 1.

Reference will now be made in detail to the preferred embodiments of the disclosed subject matter, an example of which is illustrated in the accompanying drawings. The method and corresponding steps of the disclosed subject matter will be described in conjunction with the detailed description of the system.

It is understood that the subject matter described herein is not limited to particular embodiments described, and as such may, of course, vary. It is also understood that the terminology used herein is for the purpose of describing particular embodiments only, and is not intended to be limiting, since the scope of the present subject matter is limited only by the appended claims. Where a range of values is provided, it is understood that each intervening value between the upper and lower limit of that range and any other stated or intervening value in that stated range, is encompassed within the disclosed subject matter.

FIG. 1 illustrates a balloon catheter 10 which embodies features of the invention, generally comprising an elongated catheter shaft 11 having a proximal shaft section 12, a distal shaft section 13, an inflation lumen 21, and a guidewire lumen 22 configured to slidably receive a guidewire 23 therein, and having a balloon 14 mounted on the distal shaft section. An adapter 17 on a proximal end of the catheter shaft provides access to the guidewire lumen 22, and has an arm 24 configured for connecting to a source of inflation fluid (not shown).

FIG. 1 illustrates the balloon in a noninflated configuration for advancement within a patient's blood vessel 18. The balloon catheter 10 is advanced in the body lumen 18 with the balloon 14 in the noninflated configuration, and the balloon inflated by introducing inflation fluid into the balloon interior to expand the balloon 14.

In the illustrated embodiment, the shaft 11 comprises an outer tubular member 19 defining the inflation lumen 21, and an inner tubular member 20 defining the guidewire lumen 22 and positioned in the outer tubular member 19 such that the inflation lumen 21 is the annular space between the inner surface of the outer tubular member 19 and the outer surface of the inner tubular member 20, as best shown in FIG. 2 illustrating a transverse cross section of the catheter of FIG. 1, taken along line 2-2. The balloon 14 has a proximal skirt section sealingly secured to the distal end of the outer tubular member 19, and a distal skirt section sealingly secured to a distal end of the inner tubular member 20, so that an interior 15 of the balloon is in fluid communication with the inflation lumen 21 of the shaft. FIG. 3 illustrates a transverse cross section of the catheter of FIG. 1, taken along line 3-3, although the space between the inner surface of the noninflated balloon and the outer surface of the portion of the shaft 11 therein is somewhat exaggerated in FIG. 1 and FIG. 3, for ease of illustration. A variety of alternative suitable catheter shaft configurations can be used as are conventionally known.

Balloon 14 can be formed in various shapes. As shown in FIG. 4, the shape of balloon 14 is substantially cylindrical. However, the shape of balloon 14 can be spherical, cylindrical, or polygonal. Various polymers may be selected for the formation of balloon 14, as would be known in the art. However, the balloon material should be sufficiently compliant such that balloon 14 can mold to the shape of the blood vessel.

In accordance with another aspect of the disclosed subject matter, a medical device configured for localized delivery of a therapeutic agent comprises a balloon 14 with fibers 402 extending outwardly from the exterior surface of balloon 14. As the balloon is inflated using the inflation fluid containing the therapeutic agent, e.g. sclerosing agent, the therapeutic agent diffuses through pores in the balloon. The therapeutic agent is guided to the wall of the blood vessel by the fibers 402. In some embodiments, this may occur via capillary action. In other embodiments, the fibers 402 are elongate and hollow. Thus, the therapeutic agent is delivered directly to the wall of the blood vessel through the hollow fibers 402. The balloon 14 may be moved within the vein to brush against the blood vessel wall, similar to the action of a bottle brush. The fibers 402 can be formed with sufficient flexibility so as to prevent damage to the intima of the blood vessel. Such malleable fibers can be advantageous in protecting the integrity of vessel wall so as to prevent piercing or puncture through the vessel wall, which can result in leakage of blood out into tissue as well as subjecting the patient to unnecessary and undesired pain. Additionally, the fibers 402 can exhibit sufficient rigidity to remove blood adhered to the inner surface of the vessel wall so as to wipe clean the desired surface area in order to accelerate or enhance the efficacy of the therapeutic agent and simultaneously shorten the duration of the procedure. Additionally, the fibers 402 can be attached to the balloon in a variety of ways including welding or via an adhesive bond.

For purpose of illustration and not limitation, Sclerosing agents compatible with the present invention include, but are not limited to, alcohols such as ethanol or polidocanol (POL), as well as sodium tetradecyl sulphate (STS), Sclerodex, hypertonic saline, glycerin and chromated glycerin, or combinations thereof. These sclerosing agents have been found to effect the cellular responses to growth stimulation and cause the vessel walls to immediately shrink upon exposure to the agents. While specific examples of sclerosing agents are described herein, it is to be understood that alternative therapeutic agents can be administered to the vessel wall utilizing the device and methods disclosed herein. Accordingly, as used herein, a "therapeutic agent" includes any agent that promotes health, recovery or diagnosis. For example, the therapeutic agent may be a drug, protein, or contrast agent. Preferably, the balloon 14 is constructed of biodegradable materials. To aid in the distribution of the sclerosing agent, the surface of balloon 14 is blood phobic and/or alcohol phylic. In some embodiments, balloon 14 may include perforations through the wall of the balloon. Preferably, the perforations are approximately 20 microns in diameter. These holes can be arranged in a uniform pattern along the length of the balloon, or alternatively, be configured in a predetermined varied density pattern such that the balloon exhibits a varied porosity. For example, the balloon can be configured with a greater number of pores at one end to provide for a higher concentration of agent delivered to localized areas of the vessel wall. Preferably, the location of the holes and anchor or attachment point of the fibers 402 are proximate each other to facilitate the distribution of the therapeutic agent via capillary action along the fiber and onto the surface of the vessel wall. In some embodiments, hollow fibers 402 can be employed and disposed at locations which coincide with the pores formed in the balloon. Further, to aid in the capillary action, the fibers 402 can constructed of a material which is blood phobic and alcohol phylic.

Figure 5:
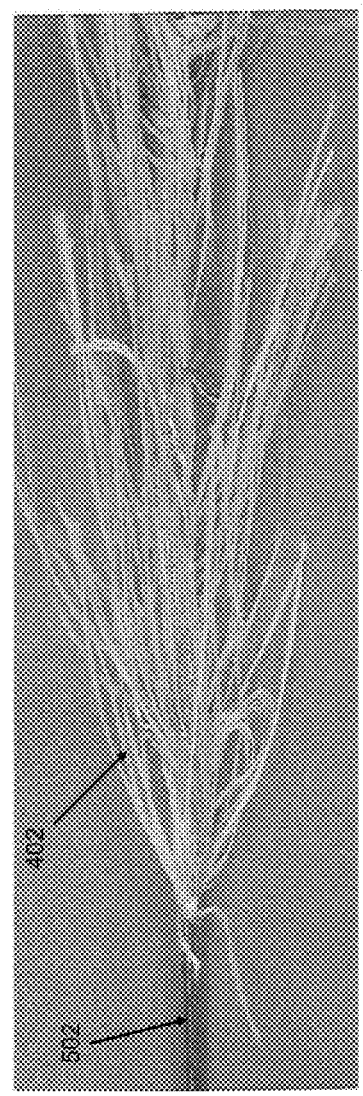
FIG. 5 illustrates a balloon with fibers for use with a capture sheath.

As shown in FIG. 5, the balloon 14 may be covered by a capture sheath 502 prior to inflation. The capture sheath serves to keep fibers 402 confined close to the surface of balloon 14 to facilitate delivery of the device to the desired location within the vessel. The capture sheath 502 can then be slidably removed or retracted from the balloon 14 prior to inflation and subsequently advanced over the fibers after deflation of the balloon.

Figure 6:
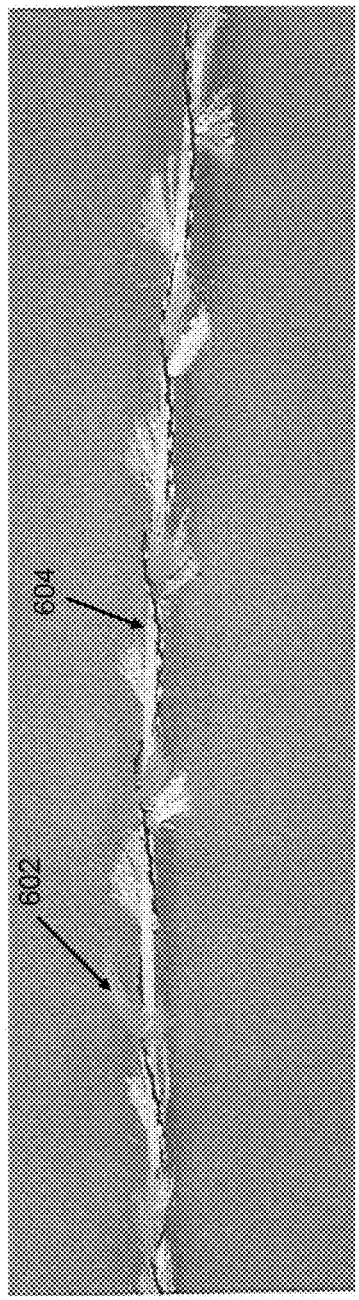
FIG. 6 illustrates a balloon having an external sheath with fibers.
Figure 7:
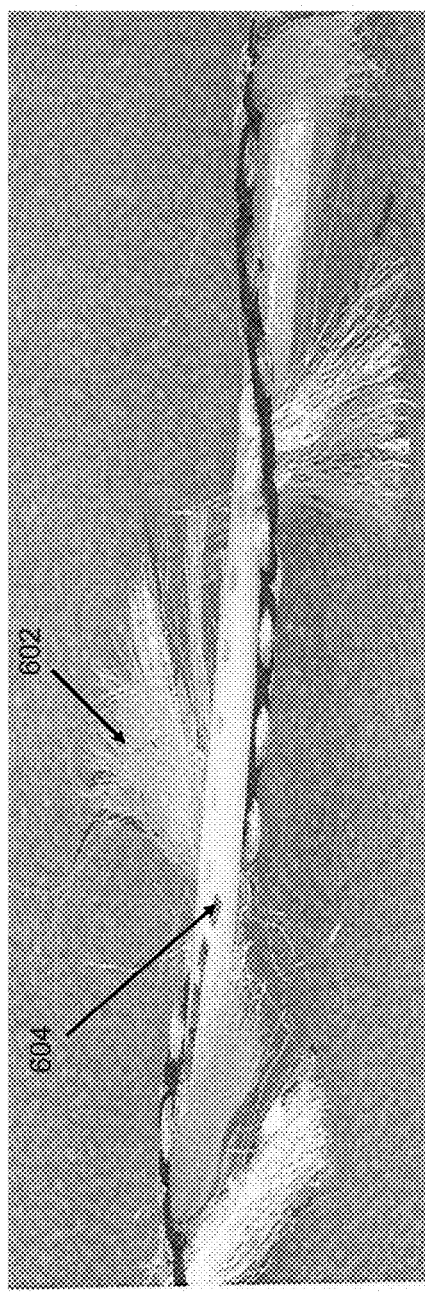
FIG. 7 illustrates an enhanced view of the balloon of FIG. 6.

In another embodiment of the disclosed subject matter, the hollow fibers 602 may be disposed on a sheath 604 that is disposed on the surface of balloon 14 as shown in FIG. 6 and FIG. 7. In this embodiment, balloon 14 may be formed with a smooth exterior surface and not contain fibers. The sheath and/or fibers can be distributed along any desired length of the balloon, and in any particular pattern, as described above. As balloon 14 is inflated/deflated, sheath 604 is also inflated/deflated, respectively. The sclerosing agent diffuses through the surface of the balloon 14 and sheath 604 as balloon 14 is inflated. The sclerosing agent is then carried to the surface of the blood vessel via fibers 602. Sheath 604 is preferably formed from an elastomeric and/or biodegradable material, such that it is capable of expanding as balloon 14 expands. Additionally, a variety of sheath sizes and fiber patterns/concentrations can be employed for any given balloon size. This allows for greater flexibility and customization according to the particular patient's needs.

Depending upon the requirements of balloon 14, it may be formed from a compliant and/or a non-compliant material. Examples of a compliant material include, but are not limited to, silicone, thermoplastic elastomer (TPE), or a polyamide/polyether block copolymer (commonly referred to as PEBA or polyether-block-amide). Preferably, the polyamide and polyether segments of the block copolymers may be linked through amide or ester linkages. The polyamide block may be selected from various aliphatic or aromatic polyamides known in the art. Preferably, the polyamide is aliphatic. Some non-limiting examples include nylon 12, nylon 11, nylon 9, nylon 6, nylon 6/12, nylon 6/11, nylon 6/9, and nylon 6/6. Preferably, the polyamide is nylon 12. The polyether block may be selected from various polyethers known in the art. Some non-limiting examples of polyether segments include poly(tetramethylene glycol), tetramethylene ether, polyethylene glycol, polypropylene glycol, poly(pentamethylene ether) and poly(hexamethylene ether). Commercially available PEBA material may also be utilized such as for example, PEBAX® materials supplied by Arkema (France). Various techniques for forming a balloon from highly compliant material are known in the art. One such example is disclosed in U.S. Pat. No. 6,406,457 to Wang, the disclosure of which is incorporated by reference in its entirety.

The compliant material may be crosslinked or uncrosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure.

Examples of low or non-compliant balloon materials include low tensile set polymer such as a polyvinyl chloride, polyethylene teraphthalate, nylon, Pebax, silicone-polyurethane copolymer. Preferably, the silicone-polyurethane is an ether urethane and more specifically an aliphatic ether urethane such as PURSIL AL 575A and PURSIL AL10 (Polymer Technology Group), and ELAST-EON 3-70A (Elastomedics), which are silicone polyether urethane copolymers, and more specifically, aliphatic ether urethane cosiloxanes.

In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. The diene polymer can be an isoprene including isoprene copolymers and isoprene block copolymers such as poly(styrene-block-isoprene). A presently preferred isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers.

In another embodiment, the balloon material is formed from polyamides. Preferably, the polyamide has substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference in its entirety. Some non-limiting examples of polyamide materials suitable for the balloon include nylon 12, nylon 11, nylon 9, nylon 69 and nylon 66. Preferably, the polyamide is nylon 12. In yet another embodiment, balloon 14 is composed of several different layers, each one being a different polyamide or polyamide/polyether block copolymer.

In accordance with some embodiments, balloon 14 can be composed of a single polymeric layer, or alternatively, can be a multilayered balloon, such as those described in U.S. Pat. No. 5,478,320 to Ishida, U.S. Pat. No. 5,879,369 to Trotta, or U.S. Pat. No. 6,620,127 to Lee, the disclosures of which are incorporated herein by reference in their entirety.

Figure 8:
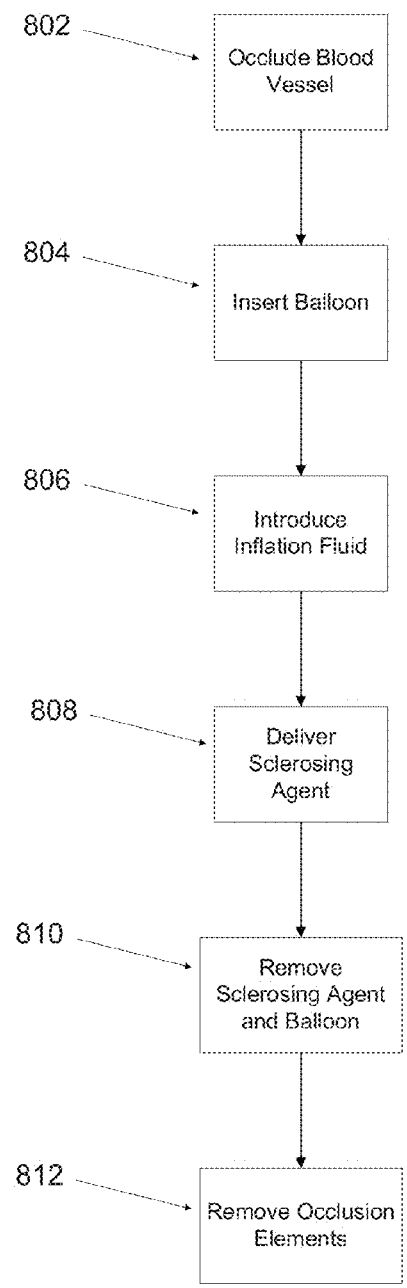
FIG. 8 illustrates a flowchart depicting a method for performing sclerotherapy.

A method of performing sclerotherapy in accordance with the presently described subject matter is also included herein. Now, with reference to FIG. 8, a flowchart is provided illustrating steps for performing sclerotherapy using the different embodiments of the device described herein. First, the desired portion of the blood vessel is occluded using one or more occlusion elements at 802. The space between the occlusion elements in the blood vessel defines the region for performing sclerotherapy. In some embodiments, the occluding elements may include a balloon, a gel, a bellows, or a permanent occlusion device. In other embodiments, the occlusion elements may be self expanding.

Next, the balloon having fibers extending laterally from the balloon is inserted into the occluded portion at 804. The inflation fluid, including the sclerosing agent, can then be introduced into the balloon, causing it to inflate at 806. The sclerosing agent is introduced to the walls of the blood vessel through the tips of the fibers at 808.

After the sclerosing agent has been imparted to the walls of the blood vessel, the sclerosing agent and balloon are removed from the blood vessel at 810 and the occlusion elements are removed at 812. To aid the sclerotherapy, a bandage or wrap may be used to compress the blood vessel to promote necrosis.

While the disclosed subject matter is described herein in terms of certain preferred embodiments, those skilled in the art will recognize that various modifications and improvements may be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment may be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A balloon catheter comprising:
   a catheter having at least one lumen extending therethrough;
   a balloon having a body including an inner surface and an outer surface defining a balloon wall, wherein the body defines an interior volume in fluid communication with the at least one lumen and having an unexpanded configuration and an expanded configuration; and
   a plurality of fibers extending from the outer surface of the balloon wall, wherein the fibers are sufficiently malleable to prevent damage to an intima of a blood vessel.

2. The balloon catheter of claim 1, wherein the fibers are elongate and hollow.

3. The balloon catheter of claim 2, wherein the fibers are configured to deliver a therapeutic agent.

4. The balloon catheter of claim 1, wherein the balloon is constructed from biodegradable materials.

5. The balloon catheter of claim 1, wherein the outer surface of the balloon is blood phobic.

6. The balloon catheter of claim 1, wherein the outer surface of the balloon is alcohol phylic.

7. The balloon catheter of claim 1 further including an inflation fluid, wherein the inflation fluid includes a sclerosing agent.

8. The balloon catheter of claim 7, wherein the sclerosing agent is ethanol.

9. The balloon catheter of claim 1 further comprising a sheath configured to be slidable over the balloon when the balloon is in the unexpanded configuration.

10. The balloon catheter of claim 9, wherein the sheath is removable from the balloon prior to expansion.

11. The balloon catheter of claim 1, where the balloon includes perforations through the balloon wall.

12. The balloon catheter of claim 1, wherein the perforations are approximately 20 microns in diameter.

\* \* \* \* \*